(12) United States Patent
Kobzeff et al.

(10) Patent No.: US 9,101,151 B2
(45) Date of Patent: **\*Aug. 11, 2015**

(54) HIGH-QUALITY LIPIDS PRODUCED BY ENZYMATIC LIBERATION FROM BIOMASS

(75) Inventors: Joseph M. Kobzeff, Charlottesville, VA (US); Craig A. Weaver, Boulder, CO (US)

(73) Assignee: DSM IP Assets B.V., Heerlen (NL)

( * ) Notice: Subject to any disclaimer, the term of this patent is extended or adjusted under 35 U.S.C. 154(b) by 2134 days.

This patent is subject to a terminal disclaimer.

(21) Appl. No.: 10/513,576

(22) PCT Filed: May 5, 2003

(86) PCT No.: PCT/US03/14177
§ 371 (c)(1),
(2), (4) Date: Oct. 11, 2005

(87) PCT Pub. No.: WO03/092628
PCT Pub. Date: Nov. 13, 2003

(65) Prior Publication Data
US 2006/0099693 A1    May 11, 2006

Related U.S. Application Data

(60) Provisional application No. 60/377,550, filed on May 3, 2002.

(51) Int. Cl.
| | |
|---|---|
| *A23D 9/00* | (2006.01) |
| *A61K 31/202* | (2006.01) |
| *A23L 1/29* | (2006.01) |
| *A23L 1/30* | (2006.01) |
| *C11B 1/02* | (2006.01) |
| *C11B 3/00* | (2006.01) |
| *C11B 5/00* | (2006.01) |
| *C12N 1/06* | (2006.01) |
| *C12P 7/64* | (2006.01) |

(52) U.S. Cl.
CPC . *A23D 9/00* (2013.01); *A23L 1/296* (2013.01); *A23L 1/3006* (2013.01); *A23L 1/3008* (2013.01); *A61K 31/202* (2013.01); *C11B 1/025* (2013.01); *C11B 3/001* (2013.01); *C11B 5/0021* (2013.01); *C12N 1/06* (2013.01); *C12N 1/066* (2013.01); *C12P 7/6472* (2013.01); *A23V 2002/00* (2013.01)

(58) Field of Classification Search
CPC . A61K 2300/00; A61K 31/232; A61K 31/07; A61K 31/122; A61K 31/202; A61K 31/352; A61K 31/683; A61K 31/685; A61K 31/355; A61K 47/12; A61K 31/20; A61K 31/23; A61K 31/663; A61K 35/74; A61K 45/06; A61K 36/02
See application file for complete search history.

(56) References Cited

U.S. PATENT DOCUMENTS

| | | | |
|---|---|---|---|
| 5,130,242 A | 7/1992 | Barclay | |
| 5,133,963 A * | 7/1992 | Ise | 424/94.61 |
| 5,288,619 A | 2/1994 | Brown et al. | |
| 5,340,742 A | 8/1994 | Barclay | |
| 5,969,169 A | 10/1999 | Fan | |
| 6,127,185 A | 10/2000 | Melton et al. | |
| 6,201,145 B1 | 3/2001 | Fan | |
| 6,204,401 B1 | 3/2001 | Perrut et al. | |
| 6,255,505 B1 | 7/2001 | Bijl et al. | |
| 6,270,828 B1 | 8/2001 | DeBonte et al. | |
| 6,541,049 B2 | 4/2003 | Barclay | |
| 6,607,900 B2 | 8/2003 | Bailey et al. | |

FOREIGN PATENT DOCUMENTS

| | | |
|---|---|---|
| EP | 1 178 103 A1 | 2/2002 |
| EP | 1178118 A | 6/2002 |
| WO | WO0044862  * | 8/2000 |

OTHER PUBLICATIONS

Ellenbogen et al, "Polyunsat. Fatty acids of aquatic fungi: Possible Phylog. significance", Comp. Biochem, Physil., 1969, vol. 29pp. 805-811.*
Rosenthal et al "Aqueous and enzymatic processes for edible oil extraction", Enzyme and Microbial Technology, 19: 402-420, 1996.*
International Search Report for PCT/US04/34965, date of mailing Sep. 26, 2007.
Written Opinion for PCT/US04/34965, date of mailing Sep. 26, 2007.
International Search Report for International (PCT) Patent Application No. PCT/US03/14177, mailed Nov. 3, 2003.
Written Opinion for International (PCT) Patent Application No. PCT/US03/14177, mailed Jul. 1, 2004.
International Preliminary Examination Report for International (PCT) Patent Application No. PCT/US03/14177, mailed Feb. 17, 2005.

(Continued)

*Primary Examiner* — Debbie K Ware
(74) *Attorney, Agent, or Firm* — Shannon McGarrah; Xi Chen

(57) ABSTRACT

A high-quality lipid composition is disclosed having low oxidative deterioration such as measured by low anisidine values. Also disclosed are methods of preparing the same from a lipid-containing material that include enzymatic degradation of protein and/or carbohydrate components of the material. Lipid-containing materials include biomass, such as microorganisms. The invention further includes products containing the lipid compositions, such as dietary supplements, food products, pharmaceutical formulations, humanized animal milk, and infant formula.

22 Claims, No Drawings

(56) References Cited

OTHER PUBLICATIONS

International Preiliminary Examination Report for International (PCT) Patent Application No. PCT/US2004/034965, mailed Dec. 27, 2007.
Communication in Cases for Which no Other Form is Applicable, including Corrected International Search Report and Corrected Written Opinion for International (PCT) Patent Application No. PCT/US2004/034965, mailed Oct. 31, 2007.
Macfarlane, et al., Inform, 2001 12:244-249.
Akoh, C.C. and D.B. Min, ed., *Food Lipids: Chemistry, Nutrition, and Biotechnology*, pp. 208-385, New York: Marcel Dekker, Inc., 1998.
Gunstone, F.D., John L. Hardwood, and Fred B. Padley, ed., *The Lipid Handbook*, pp. 258-261, London: Chapman & Hall, 1995.
Lin, C., et al., "Efficiency of Removing Volatiles from Menhaden Oils by Refining, Bleaching, and Deodorization," *J. Food Sci.* 55: 1669-1672, Institute of Food Technologists, United States (1990).
List, G., et al., "Oxidation and Quality of Soybean Oil: A Preliminary Study of the Anisidine Test," *J. Am. Oil Chem. Soc.* 51:17-21, American Oil Chemists Society, United States (1974).
Office Action mailed Apr. 14, 2010, in U.S. Appl. No. 10/971,723, Weaver et al., filed Oct. 22, 2004.
Office Action mailed Jul. 22, 2009, in U.S. Appl. No. 10/971,723, Weaver et al., filed Oct. 22, 2004.
Office Action mailed Mar. 19, 2009, in U.S. Appl. No. 10/971,723, Weaver et al., filed Oct. 22, 2004.
Office Action mailed Dec. 15, 2008, in U.S. Appl. No. 10/971,723, Weaver et al., filed Oct. 22, 2004.
Office Action mailed Feb. 21, 2008, in U.S. Appl. No. 10/971,723, Weaver et al., filed Oct. 22, 2004.
Office Action mailed Jul. 3, 2007, in U.S. Appl. No. 10/971,723, Weaver et al., filed Oct. 22, 2004.
Extended European Search Report for European Patent Application No. 10 17 7024.6, European Patent Office, Munich, Germany mailed Nov. 24, 2010.

* cited by examiner

HIGH-QUALITY LIPIDS PRODUCED BY ENZYMATIC LIBERATION FROM BIOMASS

REFERENCE TO RELATED APPLICATION

This application claims the benefit of priority under 35 U.S.C. §119(e) from U.S. Provisional Application Ser. No. 60/377,550, filed May 3, 2002, which is incorporated herein by reference in its entirety.

FIELD OF THE INVENTION

The present invention is directed to high-quality lipids, and in particular, lipids with low anisidine values. Methods are provided for producing high-quality lipids that include the step of liberating lipids from biomass, such as algal biomass, using enzymatic treatment.

BACKGROUND OF THE INVENTION

Various methods have been employed for extracting lipids from biomass. Techniques include direct extraction of the biomass with solvents, heating, pressure waves generated via electric arcs, direct saponification via KOH and ethanol, sonication, freezing and grinding and bead mills. For example, the biomass can be dried and the lipid extracted with a solvent such as hexane. Alternatively, a microbial fermentation broth can be subjected to extreme conditions of pH and/or temperature or additional equipment such as a homogenizer can be used to disrupt the cells.

Problems with prior methods include poor product quality due to chemically aggressive conditions of high temperature and high pH, high costs due to the need to dry the biomass or for additional equipment such as homogenizers and pressure vessels.

The "fishy" and "painty" flavors associated with many polyunsaturated fatty acids (PUFAs) found in lipids are primarily due to oxidation of the double bonds in the fatty acids. These flavor and odor notes are normally considered defects that can preclude their use in foods or other applications. The oxidative state and stability of a lipid or lipid-containing material can be measured in a number of ways. Standard measurement techniques include "anisidine value," "peroxide value," "oxidative stability index," "Rancimat," and gas chromatograph headspace analysis for oxidation products. Information on these different techniques is available from the AOCS (American Oil Chemists' Society) as well as from other sources.

The oxidative state of the lipid or lipid-containing material is strongly impacted by the processing conditions used to make the material. For food materials, the conditions during processing as well as the actual ingredients and quality of the ingredients will affect the oxidation state. For fermentation-derived lipids (e.g., lipids obtained from microbes grown in fermentors, ponds, etc.), the ingredients (fermentation and post-fermentation) used as well as the conditions during the lipid extraction and fermentation will affect the quality. Other sources of PUFAs, such as agricultural crops and animal sources, will also be affected by the processing conditions used to obtain the lipids and lipid-containing materials.

SUMMARY OF THE INVENTION

The present application is directed toward a lipid comprising polyunsaturated fatty acid wherein the lipid has an anisidine value of 2 or less, and in various embodiments the anisidine value can be as low as 0.3 or less. The polyunsaturated fatty acid in the lipid can be a long chain polyunsaturated fatty acid, having a chain length of at least 20 or at least 22, and can have at least three or at least four double bonds. More particularly, the polyunsaturated fatty acid can be docosahexaenoic acid, docosapentaenoic acid, or arachidonic acid.

The lipid can be obtained from biomass, for example, from a plant or microorganism. For example, the lipid can be obtained from algae, bacteria, fungi or protists. In preferred embodiments, the lipid can be obtained from microorganisms of the genus *Mortierella*, genus *Crypthecodinium*, or order Thraustochytriales. Further, the lipid can comprise a monoacylglyceride, a diacylglyceride, or a triacylglyceride.

Further embodiments of the present invention include products selected from dietary supplements, food products, pharmaceutical formulations, humanized animal milk or infant formula wherein the products include a lipid comprising polyunsaturated fatty acid and having an anisidine value of 2 or less.

A further embodiment of the present invention is a method of obtaining a polyunsaturated fatty acid-containing lipid which includes providing a biomass containing a polyunsaturated-containing fatty acid, contacting the biomass with an enzyme, and recovering the lipid.

A further method of the present invention is a method for liberating a lipid from a biomass comprising liberating the lipid at a temperature of about 10 C to about 80 C at a pH level of from about pH 5 to about pH 9. This method is conducted in the substantial absence of an extraction solvent.

DETAILED DESCRIPTION OF THE INVENTION

In accordance with one embodiment of the present invention, a high-quality lipid is provided. In particular, the lipid has a low anisidine value. Preferably, the anisidine value is 2 or less, more preferably 1.5 or less, more preferably 1 or less, more preferably 0.5 or less and more preferably 0.3 or less. Anisidine value can be thought of as a measure of the oxidative history of a lipid. Higher values indicate a lipid that has experienced more oxidative stress. As a lipid is oxidized, it is typically converted to a peroxide. This peroxide typically gets converted to an aldehyde or ketone. The anisidine value is a measure of these secondary oxidation products. Polyunsaturated fatty acid-containing lipids are very sensitive to oxidation and this oxidation can lead to off-flavors. Methods have been employed to remove these off-flavors, but these methods do not remove all of the oxidation products that can then act as off-flavor, and oxidation, precursors. As a result, these flavor improvement methods only lead to temporary improvement of the flavor. The anisidine value is a measurement of these oxidation and off-flavor precursors. The analytical method for measuring anisidine value is available from the AOCS (American Oil Chemists' Society).

In accordance with another embodiment of the present invention, a process for liberating lipids is provided. The process includes a step of liberating lipids using an enzymatic treatment for, e.g., degradation of cell walls of the lipid-containing material. Preferably, the lipids are liberated from a lipid-containing biomass using a protease enzyme whereby protein components of the lipid-containing material are proteolyzed, or other enzyme that is appropriate for breaking down or reacting with the lipid-containing material.

A further embodiment of the present invention is a process that utilizes surfactants in addition to the enzymes to liberate the lipids from the lipid-containing material. The inventors have surprisingly found that the use of surfactants together with enzymatic treatment can allow for milder reaction conditions than with enzymes alone for liberation of the lipids. Surfactants, such as Polysorbate 80, mono- and diglycerides, or other surfactants, are preferably added at approximately the same time as the enzyme. Alternatively, surfactant can be added before or after the enzyme. In this embodiment, the lipid is preferably liberated from the biomass without using extreme conditions of temperature or pH and without using additional equipment such as a homogenizer or drying the biomass prior to lipid removal. For example, the enzymatic treatment can be conducted at temperatures below about 80 C, more preferably below about 70 C, and even more preferably, below about 65 C, and at pH conditions of approximately 5-9.

The use of protease enzymes, or protease enzymes in combination with surfactants, provides an economical and simple way of releasing the lipid from the biomass under mild conditions conducive to making high-quality lipid. The lipid can then be isolated from the rest of the fermentation broth by centrifugation of the mixture. In some cases, the lipid will be incorporated into an emulsion. For some applications, the emulsion itself might be the final product For other applications, the emulsion would be treated to release the lipid for recovery separately. Techniques are taught in U.S. patent application Ser. No. 09/766,500 and include, but are not limited to, dilution, addition of a solvent, temperature shifts, and freezing.

The use of a protease enzyme can help break down emulsion-stabilizing proteins present, thereby aiding in the breaking of an emulsion. In addition, the successful use of a protease for lipid liberation from microalgae is surprising because, microalgae tend to have a low protein content (~15-22% compared to ~55% for *E. coli*), and have very robust cellular structure due to the presence of silica and polysaccharides such as cellulose.

This processing step also allows the production of lipids containing long chain polyunsaturated fatty acids (PUFAs) of exceedingly high quality as measured by anisidine value. The reason is that the process can easily be done under an inert atmosphere, with low temperatures, and non-reactive conditions.

In a particular embodiment, using proteolytic treatment of the lipid-containing material without a surfactant, the proteolytic treatment can be conducted at higher temperatures, sufficient to achieve desirable levels of lipid liberation. For example, in this embodiment, the enzymatic treatment is conducted at temperatures of at least about 30 C, more preferably at least about 40 C, and most preferably at least about 50 C. It should be recognized however, that at higher temperatures, degradation of lipids can occur. Therefore, a temperature must be selected such that adequate lipid liberation is achieved without unacceptable levels of lipid degradation.

Preferred polyunsaturated fatty acid sources can be any sources that are capable of liberation by enzymes as in the present invention. Preferred polyunsaturated fatty acids sources include biomass sources, such as animal, plant and/or microbial sources. As used herein, the term "lipid" includes phospholipids; free fatty acids; esters of fatty acids; triacylglycerols; diacylglycerides; monoacylglycerides; lysophospholipids; soaps; phosphatides; sterols and sterol esters; carotenoids; xanthophylls (e.g., oxycarotenoids); hydrocarbons; and other lipids known to one of ordinary skill in the art. Examples of animal sources include aquatic animals (e.g., fish, marine mammals, crustaceans, rotifers, etc.) and lipids extracted from animal tissues (e.g., brain, liver, eyes, etc.). Examples of plant sources include macroalgae, flaxseeds, rapeseeds, corn, evening primrose, soy and borage. Examples of microorganisms include algae, protists, bacteria and fungi (including yeast). The use of a microorganism source, such as algae, can provide organoleptic advantages, i.e., fatty acids from a microorganism source may not have the fishy taste and smell that fatty acids from a fish source tend to have. More preferably, the long-chain fatty acid source comprises algae.

Preferably, when microorganisms are the source of long-chain fatty acids, the microorganisms are cultured in a fermentation medium in a fermentor. Alternatively, the microorganisms can be cultured photosynthetically in a photobioreactor or pond. Preferably, the microorganisms are lipid-rich microorganisms, more preferably, the microorganisms are selected from the group consisting of algae, bacteria, fungi and protists, more preferably, the microorganisms are selected from the group consisting of golden algae, green algae, dinoflagellates, yeast, fungi of the genus *Mortierella* and *Stramenopiles*. Preferably, the microorganisms comprise microorganisms of the genus *Crypthecodinium* and order Thraustochytriales and filamentous fungi of the genus *Mortierella*, and more preferably, microorganisms are selected from the genus *Thraustochytrium, Schizochytrium* or mixtures thereof, more preferably, the microorganisms are selected from the group consisting of microorganisms having the identifying characteristics of ATCC number 20888, ATCC number 20889, ATCC number 20890, ATCC number 20891 and ATCC number 20892, strains of *Mortierella schmuckeri* and *Mortierella alpina*, strains of *Crypthecodinium cohnii*, mutant strains derived from any of the foregoing, and mixtures thereof. It should be noted that many experts agree that *Ulkenia* is not a separate genus from the genera *Thraustochytrium* and *Schizochytrium*. Accordingly, as used herein, the genera *Thraustochytrium* and *Schizochytrium* will include *Ulkenia*. Information regarding such algae can be found in U.S. Pat. Nos. 5,407,957, 5,130,242 and 5,340,594, which are incorporated herein by reference in their entirety.

Lipids recovered by the present invention include lipids comprising a polyunsaturated fatty acid, more particularly, a long chain polyunsaturated fatty acid, and even more particularly, a polyunsaturated fatty acid present in said lipid having a carbon chain length of at least 20 or 22. Such polyunsaturated fatty acid present can have at least 3 or at least 4 double bonds. More particularly, the polyunsaturated fatty acid can include docosahexaenoic acid (at least 10, 20, 30 or 35 weight percent), docosapentaenoic acid (at least 5, 10, 15, or 20 weight percent), and/or arachidonic acid (at least 20, 30, 40 or 50 weight percent). Polyunsaturated fatty acids include free fatty acids and compounds comprising PUFA residues, including phospholipids; esters of fatty acids; triacylglycerols; diacylglycerides; monoacylglycerides; lysophospholipids; phosphatides; etc.

For different oil-containing materials, different enzymes and reaction conditions can be employed. For these different materials, an important enzyme selection criterion is to select an enzyme that will attack and degrade a portion of the material (such as the proteins, polysaccharides, cell wall, cell outer membrane, peptidoglycan layer, cellulose, chitin, hemicellulose, lignin, lignin-related compounds, etc.) that is otherwise impeding recovery of the oil. Preferably, nonspecific protease enzymes such as trypsin, chymotrypsin, or the like are used to degrade protein components of the oil-containing materials and carbohydrase enzymes such as amylase can be used to degrade carbohydrate components of the oil-containing materials. The selection of reaction conditions, including enzyme type, enzyme concentration, temperature, pH, water activity, other reagent concentration, reaction time, etc. will depend in part on the specific enzyme and material that the lipid is being liberated from. These conditions can be readily determined from information about the enzyme (and typically available from the supplier or in the literature), or determined by somebody skilled in the art. Typical temperatures may range between approximately 20-80° C., although some special enzymes may be sufficiently active and stable for use outside of this range. Typical enzyme concentrations can be as low as 0.01% to several percent. The reaction rate is related to the enzyme concentration with higher concentrations allowing for shorter reaction times. In some situations, it may be possible to use an even lower concentration, such as when a particular enzyme is extremely active or stable or when very long reaction times may be practical.

Preferably the lipids are effectively liberated from *Schizochytrium* sp organisms by treating the cells with a protease enzyme. It is surprising that this particular class of enzymes is effective for this organism due to the relatively small amount of protein normally found in the cell wall of this organism. Lipids can be liberated from biomass, and preferably microorganisms, by treating the cells with enzymes or other agents or by other methods that attack other components of the cell wall, such as polysaccharides, or the lipid bilayer. This treatment with enzymes provides one method under mild conditions that allows for recovery of high quality lipids. Other methods for liberation of lipids that can be used, alone or in combination with enzymatic treatment, include treatment with detergents, osmotic shock, freezing/thaw cycling, autolysis, homogenization, sonication, and mild heat treatment.)

One preferred embodiment of the process of the present invention includes:

Obtaining lipid-bearing single cell organisms

Treating with protease or a combination of surfactant and protease

Separating the lipid from the broth (may be an emulsion)
  May require additional treatment with a polar organic solvent, salt, precipitating agent, another enzyme (protease or other kind), heating, cooling.

If the lipid from the above step is in the form of an emulsion, this product can be used "as is" or dried and used or treated to release the lipid from the emulsion
  Treatment can include treatment with a polar organic solvent, salt, precipitating agent, another enzyme (protease or other kind), heating, cooling, etc.

The lipid can then be dried, refined, bleached, deodorized and/or reacted as needed.

The lipid can also be treated with antioxidants and/or metal ion capturing agents (such as chelating agents, ion exchange resin, precipitating agents) at any point before, during or after the process.

As noted above, the present invention encompasses the use of a protease in the presence of a surfactant to recover lipid from a biomass. Suitable surfactants include, but are not limited to: phospholipid, lysophospholipid, monoglyceride, diglycerides, mixed glycerides, partial glycerides, soaps, fatty acids, salts of fatty acids, amines, antifoam, acids or salts of sulfonic acid, detergents, polysorbates (e.g., polyethylene sorbitan monooleate), aliphatic acids and esters, polar organic molecules, alcohols, sulfates and sulfonates, nitrogen-containing compounds (e.g. amines, amides, polyamides), phosphates (e.g. alkyl-alkylene diphosphate, tributyl phosphate), silicones (e.g. tri- and tetra-alkyl silanes, silicone polymer containing silica, dimethyl silicone polymers, methyl silicones), sulfides and thio derivatives, halogenated compounds, triacylglycerols, long chain fatty waxes (e.g. vegetable oils and waxes), mineral oils, sulfated derivative of triacylglycerols and mineral oils, bentonite, and monosodium phosphate mixed with boric acid and ethyl carbonate.

In a further embodiment, the process can be conducted with a combination of enzymes. More specifically, a protease and a lipase can be used. A lipase is an enzyme that hydrolyzes glycerides. Therefore, care needs to be taken to avoid unacceptable levels of degradation of glycerides in the lipid product. For example, a lipase will hydrolyze a triglyceride producing a free fatty acid and a diglyceride. This mechanism is believed, without intending to be bound by theory, to be beneficial to an extent because products of the enzymatic degradation function as surfactants having the benefits described above in the embodiment of the invention involving direct use of surfactants. However, there is the potential that the lipid product could be unacceptably degraded by the lipase. Therefore, additional embodiments involve the use of small amounts of lipase or conditions under which the lipase is only active a small amount of the time. Such control of lipase activity could be controlled for example, by the use of temperature sensitive enzymes or the introduction of lipase inhibitors.

In another embodiment of the present invention, the processes of the present invention are combined with further oxidation-reducing techniques, including one or more of: exclusion of air (and oxygen) and other oxidizing agents, processing with mild conditions (moderate temperature, moderate pH, short processing times, etc.), exclusion of metal ions such as copper and iron, exclusion of previously oxidized lipids (even if subsequently purified), exclusion of oxidation precursors, and the presence of antioxidant compounds (such as tocopherols, tocotrienols, BHA, carnisol, camosic acid, ascorbic acid, L-ascorbic acid esters (including L-ascorbyl palmitate, L-ascorbyl stearate, L-ascorbyl oleate), rosemary, etc. as well as esters or derivatives of these compounds), to obtain minimally oxidized lipids.

In some cases, after the lipids are liberated from the biomass, the lipids can be separated directly from the undesired materials (e.g., cellular debris), such as by centrifugation, or other appropriate methods. In other cases, an agent such as an alcohol or other polar organic solvent can be added to facilitate the separation of the liberated lipid from the other material. In still other cases, a solvent can be added that will dissolve the lipid and facilitate the separation of the liberated lipid from the other material, e.g., by solvent extraction. Techniques for separating the lipids from undesired materials can be found in U.S. Pat. No. 5,928,696, U.S. patent application Ser. No. 09/766,500, and PCT Application Numbers US01/12047 and US01/12049, all of which are incorporated herein by reference in their entirety. Another embodiment of the invention involves the use of a combination of the enzyme treatment, or the enzyme plus surfactant treatment, along with homogenization. This combination in some cases can achieve higher quality and/or higher yield than with homogenization or enzyme treatment alone. It is believed that homogenization can facilitate the enzyme reaction by allowing more intimate contact between the enzyme and its substrate. It is also believed that enzyme treatment can facilitate homogenization by weakening the cell walls and allowing the use of less extreme (pressure or shear) homogenization conditions. The use of homogenization with the enzyme or enzyme-surfactant process can allow the use of conditions that are more chemically mild than would be possible without the homogenization. In other cases, this combined process can allow use of a lower pressure (and also lower cost) homogenization.

In accordance with a further embodiment of the present invention, the processes previously described can be employed on lipid-bearing material that has been dried prior to lipid removal. While the highest quality and lowest cost process would normally be expected from material that has not been dried, there are cases where it would be advantageous to dry the material either prior to or at some intermediate point during the process, prior to lipid separation. Use of the previously described processes with drying can provide a partial improvement in quality and/or cost over processes that include drying and do not include the invented processes. Some examples of when this drying step would be appropriate are when the facility for lipid separation is located remote from the fermentation or other upstream facility, or when there are scheduling difficulties between the lipid separation facility and the upstream facility, or when the lipid-containing material must be stored prior to separating the lipid.

In one aspect of the present invention, the lipid is used in an endproduct selected from the group consisting of a dietary supplement, a food product, a pharmaceutical formulation, a humanized animal milk, and an infant formula. A pharmaceutical formulation can include, but is not limited to: an anti-inflammatory formulation, a chemotherapeutic agent, an active excipient, an osteoporosis drug, an anti-depressant, an anti-convulsant, an anti-*Helicobactor pylori* drug, a drug for treatment of neurodegenerative disease, a drug for treatment of degenerative liver disease, an antibiotic, and a cholesterol lowering formulation. In one aspect, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, schizophrenia, depression, weight maintenance and peroxisomal disorder. The following examples are provided for the purpose of illustration and are not intended to limit the scope of the present invention.

EXAMPLES

Example 1

*Schizochytrium* sp. fermentation broth was diluted and buffered as follows: 25 ml of broth was combined with 65 ml DI water, then 10 ml of pH 6.0 buffer (1.0 M 2-[N-morpholino]ethanesulfonic acid) was added.

To different aliquots of this broth mixture different combinations of enzyme and surfactant were added. After the enzyme and surfactant additions, the samples were incubated at 45 C for 1.5 hr, and then examined by microscope for degree of lysis. The results are shown below:

| Enzyme* | Surfactant | Degree of lysis |
| --- | --- | --- |
| None | Polysorbate 80 | No lysis |
| Viscozyme ® L | Polysorbate 80 | No lysis |
| Alcalase ® 2.4 L FG, Viscozyme ® L | Polysorbate 80 | Mostly lysed |
| Alcalase ® 2.4 L FG | Polysorbate 80 | Virtually all lysed |
| Viscozyme ® L | None | No lysis |
| Alcalase ® 2.4 L FG | None | Mostly unlysed |

*The enzymes are both from Novozymes North America, Inc. of Franklinton, NC.

This example demonstrates both the successful lysis of the organism with enzymes and the improvement of lysis with the inclusion of a surfactant, Polysorbate 80.

Example 2

*Schizochytrium* sp. fermentation broth was diluted and buffered as in Example 1.

A commercial protease (Alcalase® 2.4 L FG, available from Novozymes North America, Inc. of Franklinton, N.C.) and a commercial carbohydrase (Viscozyme® L, available from Novozymes North America, Inc. of Franklinton, N.C.) were added to the diluted and buffered broth. This broth mixture was divided and different surfactants were added as follows:
 1. Polysorbate 80
 2. Sodium lauryl sulfate
 3. Mono and diglycerides (Dimodan CO-K from Danisco of New Century, Kans.)

After the surfactant addition, each sample was heated in a hot water bath (75 C) for approx. 5 min. Each sample was then held overnight at room temperature with mixing on a Fisher Hematology/Chemistry Mixer. The samples were examined under a microscope for degree of lysis. The results are shown below:

| Surfactant | Degree of lysis |
| --- | --- |
| Polysorbate 80 | ~100% |
| Sodium lauryl sulfate | ~40-60% |
| Dimodan CO—K | ~100% |

This example demonstrates that different surfactants can be used. In this case both Polysorbate 80 and mono and diglycerides (Dimodan) were successful. Sodium lauryl sulfate was not as successful due to this particular chemical attacking the enzymes.

Example 3

*Schizochytrium* sp. fermentation broth was treated with antioxidants (ascorbyl palmitate and tocopherols) and drum dried. This dried biomass was then treated as follows:
 Added to distilled water (51 g of biomass to 300 g water)
 The pH was adjusted to the range of 6.9-7.3 with 2N $H_2SO_4$
 The mixture was heated to 60 C in a water bath
 1.5 ml of Alcalase 2.4 L FG was added
 The broth mixture was then purged with nitrogen to exclude oxygen and incubated at 60 C for 15 hours
 120 ml of isopropanol (99.9%) was added with gentle mixing
 The broth-alcohol mixture was then centrifuged at 4000 RPM for 5 minutes
 The lipid phase (supernatant) was collected
 The collected lipid was tested for anisidine and peroxide value per AOCS (American Oil Chemists Society) methods Cd 8-53 and Cd 18-90.

A sample of the dried biomass was also hexane extracted by combining with hexane and ball milled in a Swedish tube extraction system. The lipid collected was tested for anisidine value and peroxide value as the other lipid sample. The test results of the lipid collected by the two methods are shown below:

| Sample | Peroxide Value | Anisidine Value |
| --- | --- | --- |
| Enzyme, isopropanol method | <0.1 | 0.8 |
| Hexane extracted | <0.1 | 3.0 |

This example demonstrates the successful lysis of the cells with enzymes, the isolation of the lipid that was present in the cells and the very high quality of the lipid (very low anisidine value).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A refined, bleached, or deodorized microbial or plant lipid comprising polyunsaturated fatty acid, wherein said lipid has an anisidine value of 1.5 or less, wherein said lipid has been liberated from biomass enzymatically and through addition of a surfactant, and wherein said polyunsaturated fatty acid present in said lipid comprises at least 20 weight percent docosahexaenoic acid, at least 5 weight percent docosapentaenoic acid, or at least 20 weight percent arachidonic acid.

2. The lipid of claim 1, wherein said polyunsaturated fatty acid is docosahexaenoic acid.

3. The lipid of claim 1, wherein said polyunsaturated fatty acid is docosapentaenoic acid.

4. The lipid of claim 1, wherein said polyunsaturated fatty acid is arachidonic acid.

5. The lipid of claim 1, wherein said polyunsaturated fatty acid comprises at least 30 weight percent docosahexaenoic acid.

6. The lipid of claim 1, wherein said polyunsaturated fatty acid comprises at least 35 weight percent docosahexaenoic acid.

7. The lipid of claim 1, wherein said polyunsaturated fatty acid comprises at least 10 weight percent docosapentaenoic acid.

8. The lipid of claim 1, wherein said polyunsaturated fatty acid comprises at least 15 weight percent docosapentaenoic acid.

9. The lipid of claim 1, wherein said polyunsaturated fatty acid comprises at least 20 weight percent docosapentaenoic acid.

10. The lipid of claim 1, wherein said polyunsaturated fatty acid comprises at least 30 weight percent arachidonic acid.

11. The lipid of claim 1, wherein said polyunsaturated fatty acid comprises at least 40 weight percent arachidonic acid.

12. The lipid of claim 1, wherein said polyunsaturated fatty acid comprises at least 50 weight percent arachidonic acid.

13. The lipid of claim 1, wherein said lipid is obtained from at least one of the group consisting of algae, bacteria, fungi and protists.

14. The lipid of claim 1, wherein said lipid is obtained from algae.

15. The lipid of claim 1, wherein said lipid is obtained from microorganisms selected from the group consisting of golden algae, green algae, dinoflagellates, yeast, fungi of the genus *Mortierella*, and *Stramenopiles*.

16. The lipid of claim 1, wherein said lipid is obtained from microorganisms selected from the group consisting of the genus *Mortierella*, genus *Crypthecodinium*, and order Thraustochytriales.

17. The lipid of claim 1, wherein said lipid is obtained from microorganisms selected from the group consisting of the genus *Thraustochytrium*, genus *Schizochytrium* or mixtures thereof.

18. The lipid of claim 1, wherein said lipid comprises a monoacylglyceride.

19. The lipid of claim 1, wherein said lipid comprises a diacylglyceride.

20. The lipid of claim 1, wherein said lipid comprises a triacylglyceride.

21. A product selected from the group consisting of dietary supplement, food product, pharmaceutical formulation, humanized animal milk, and infant formula, wherein the product comprises the lipid of claim 1.

22. A method of making a product selected from the group consisting of a dietary supplement, food product, pharmaceutical formulation, humanized animal milk, and infant formula, comprising adding the lipid of claim 1 to the dietary supplement, food product, pharmaceutical formulation, humanized animal milk, or infant formula.

* * * * *